United States Patent
Sherwood et al.

(10) Patent No.: US 10,083,798 B2
(45) Date of Patent: Sep. 25, 2018

(54) SINTERED ELECTRODES FOR CAPACITOR ANODES, CATHODES, ANODE SYSTEMS, AND CATHODE SYSTEMS

(71) Applicant: Cardiac Pacemakers, Inc., St. Paul, MN (US)

(72) Inventors: Gregory J. Sherwood, North Oaks, MN (US); Peter Jay Kuhn, St. Paul, MN (US); Jaymes Olson, Roseville, MN (US); Matthew Anderson, Coon Rapids, MN (US); Brian V. Waytashek, Lino Lakes, MN (US); Aaron Floeter, Waconia, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 21 days.

(21) Appl. No.: 15/267,534

(22) Filed: Sep. 16, 2016

(65) Prior Publication Data

US 2017/0076873 A1 Mar. 16, 2017

Related U.S. Application Data

(60) Provisional application No. 62/219,273, filed on Sep. 16, 2016.

(51) Int. Cl.
*A61N 1/39* (2006.01)
*H01G 9/052* (2006.01)
(Continued)

(52) U.S. Cl.
CPC ............ *H01G 9/052* (2013.01); *A61N 1/378* (2013.01); *A61N 1/3975* (2013.01); *H01G 9/008* (2013.01);
(Continued)

(58) Field of Classification Search
CPC ...... H01G 9/052; H01G 9/0029; H01G 9/008; H01G 9/02; H01G 9/028; H01G 9/06;
(Continued)

(56) References Cited

U.S. PATENT DOCUMENTS

| 6,679,926 B1 * | 1/2004 | Kajiura | H01M 4/0402 264/614 |
| 2003/0099884 A1 * | 5/2003 | Chiang | G02F 1/1523 429/233 |

(Continued)

FOREIGN PATENT DOCUMENTS

| EP | 1568052 B1 | 1/2008 |
| WO | WO-2017049061 A1 | 3/2017 |

OTHER PUBLICATIONS

"International Application Serial No. PCT/US2016/052093, International Search Report dated Jan. 5, 2017", 4 pgs.

(Continued)

*Primary Examiner* — Scott Getzow
(74) *Attorney, Agent, or Firm* — Schwegman Lundberg & Woessner, P.A.

(57) ABSTRACT

A capacitor case sealed to retain electrolyte; a sintered anode disposed in the capacitor case, the sintered anode having a shape wherein the sintered anode includes a mating portion; a conductor coupled to the sintered anode, the conductor sealingly extending through the capacitor case to a terminal disposed on an exterior of the capacitor case; a sintered cathode disposed in the capacitor case, the sintered cathode having a shape that mates with the mating portion of the sintered anode such that the sintered cathode matingly fits in the mating portion of the sintered anode; a separator between the sintered anode and the sintered cathode; and a second terminal disposed on the exterior of the capacitor case and in electrical communication with the sintered (Continued)

cathode, with the terminal and the second terminal electrically isolated from one another.

17 Claims, 8 Drawing Sheets

(51) Int. Cl.
| | |
|---|---|
| *H01G 9/10* | (2006.01) |
| *H01G 9/145* | (2006.01) |
| *H01G 9/02* | (2006.01) |
| *H01G 9/008* | (2006.01) |
| *H01G 9/28* | (2006.01) |
| *H01G 9/00* | (2006.01) |
| *H01G 9/028* | (2006.01) |
| *H01G 9/06* | (2006.01) |
| *H01G 9/15* | (2006.01) |
| *A61N 1/378* | (2006.01) |
| *H01G 9/04* | (2006.01) |

(52) U.S. Cl.
CPC .............. *H01G 9/0029* (2013.01); *H01G 9/02* (2013.01); *H01G 9/028* (2013.01); *H01G 9/06* (2013.01); *H01G 9/10* (2013.01); *H01G 9/145* (2013.01); *H01G 9/15* (2013.01); *H01G 9/28* (2013.01); *H01G 2009/05* (2013.01)

(58) Field of Classification Search
CPC ............ H01G 9/10; H01G 9/145; H01G 9/15; H01G 9/28; A61N 1/378; A61N 1/3975
See application file for complete search history.

(56) References Cited

U.S. PATENT DOCUMENTS

| | | | |
|---|---|---|---|
| 2006/0023400 A1* | 2/2006 | Sherwood | ............ H01G 9/0032 361/503 |
| 2006/0028787 A1 | 2/2006 | Yoshida et al. | |
| 2007/0211413 A1 | 9/2007 | Fife et al. | |
| 2008/0170353 A1 | 7/2008 | Swanson et al. | |
| 2011/0152961 A1 | 6/2011 | Sherwood | |
| 2016/0189876 A1* | 6/2016 | Djebara | ................. H01G 9/048 607/119 |

OTHER PUBLICATIONS

"International Application Serial No. PCT/US2016/052093, Written Opinion dated Jan. 5, 2017", 6 pgs.

* cited by examiner

SINTERED ELECTRODES FOR CAPACITOR ANODES, CATHODES, ANODE SYSTEMS, AND CATHODE SYSTEMS

CLAIM OF PRIORITY

This application claims the benefit of priority under 35 U.S.C. § 119(e) of U.S. Provisional Patent Application Ser. No. 62/219,273, filed on Sep. 16, 2015, which is herein incorporated by reference in its entirety.

TECHNICAL FIELD

This document relates generally to energy storage and particularly to sintered electrodes to store energy in an implantable medical device.

BACKGROUND

Electrical stimulation therapy has been found to benefit some patients. For example, some patients suffer from an irregular heartbeat or arrhythmia and may benefit from application of electrical stimulation to the heart. Some patients suffer from a particular type of arrhythmia called a fibrillation. Fibrillations may affect different regions of the heart, such as the atria or the ventricles. When a fibrillation occurs in the ventricles, the heart's ability to pump blood is dramatically reduced, putting the patient at risk of harm. It has been found that applying an electrical stimulation to the patient can effectively treat patients suffering disorders such as from fibrillation by restoring a regular heartbeat.

Because disorders such as fibrillations can happen at any time, it is helpful to have a device that is easily accessible to treat them. In some cases, it is helpful if that device is portable or implantable. In developing a device that is portable or implantable, it is helpful to have access to components that are compact and lightweight and that can perform to desired specifications.

SUMMARY

In example 1, an apparatus including a capacitor case sealed to retain electrolyte; a sintered anode disposed in the capacitor case, the sintered anode having a shape wherein the sintered anode includes a mating portion; a conductor coupled to the sintered anode, the conductor sealingly extending through the capacitor case to a terminal disposed on an exterior of the capacitor case; a sintered cathode disposed in the capacitor case, the sintered cathode having a shape that mates with the mating portion of the sintered anode such that the sintered cathode matingly fits in the mating portion of the sintered anode; a separator between the sintered anode and the sintered cathode; and a second terminal disposed on the exterior of the capacitor case and in electrical communication with the sintered cathode, with the terminal and the second terminal electrically isolated from one another.

In example 2, the subject matter of example 1 can optionally include the sintered anode having a non-rectangular shape.

In example 3, the subject matter of example 1 or 2 can optionally include the sintered cathode having a non-rectangular shape.

In example 4, the subject matter of any of examples 1-3 can optionally include the mating portion of the sintered anode being a void space shaped like a fin and the sintered cathode having a fin shape.

In example 5, the subject matter of any of examples 1-4 can optionally include the mating portion of sintered anode being rounded cut-outs at one or more corners of the sintered anode.

In example 6, the subject matter of example 5 can optionally include the sintered cathode having a cylindrical shape In example 7, the subject matter of example 6 can optionally include the sintered anode having a triangular shape with the rounded cut-outs at the three corners of the triangular shape.

In example 8, the subject matter of example 7 can optionally include a plurality of sintered anodes having triangular shapes and arranged together in a side by side configuration with a plurality of cylindrical cathodes located at the rounded out corners of each of the plurality of sintered anodes.

In example 9, the subject matter of any of claims 1-8 can optionally include the separator being a high dielectric polymer directly applied to an outer surface of the sintered cathode.

In example 10, the subject matter of any of examples 1-9 can optionally include the sintered cathode having a high capacitance coating on an outer surface.

In example 11, the subject matter of any of examples 1-10 can optionally include the cathode having a bed of nails structure.

In example 12, the subject matter of any of examples 1-11 can optionally include the mating portion being conical and the sintered cathode being conical.

In example 13, the subject matter of any of examples 1-12 can optionally include the sintered anode and the sintered cathode being standalone slugs that include the sintered portion, with the sintered portion being monolithic.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

This document concerns sintered electrodes for use in an electrical energy storage device. Specific examples include sintered anodes formed of aluminum or its alloys. Some examples use sintered anodes formed of tantalum. Certain examples are for use in aluminum electrolytic capacitors. Additional benefits stem from an increased surface area that is a product of sintering.

Sintering results in many interstices (i.e., spaces) between grains of the electrode. Sintered electrodes resemble crushed grains with interstices between the grains. The interstices are filled with electrolyte, thereby increasing capacitance per unit of volume, as capacitance is proportional to a surface area exposed to electrolyte. An electrode with such interstices offers improved lateral or parallel movement of electrons in relation to a major surface of a flat electrode layer, as etched electrodes restrict lateral movement because the etchings result in voids that are typically perpendicular to the major surface of the flat layer. Accordingly, some examples have a lower ESR (equivalent series resistance) compared to etched foils due to this enhance ionic flow.

Overall, an energy storage device using the sintered electrodes described here is well suited for use in an implantable medical device such as a defibrillator. Because sintering can produce a variety of shapes, sintered electrodes can be used to create energy storage devices such as capacitors that have custom shapes versus simple rolled cylinders or a prism having a parallelogram as its base. Further, manufacturing efficiency is improved, by easing the steps and parts in manufacturing a capacitor and by reducing waste. The interstices are very small, making the electrodes rigid and able to withstand handling by a machine or assembly personnel. These electrodes demonstrate an improved energy density over etched electrodes and are therefore useful to make smaller implantable devices that are able to deliver an amount of energy for a particular therapy.

Figure 1:
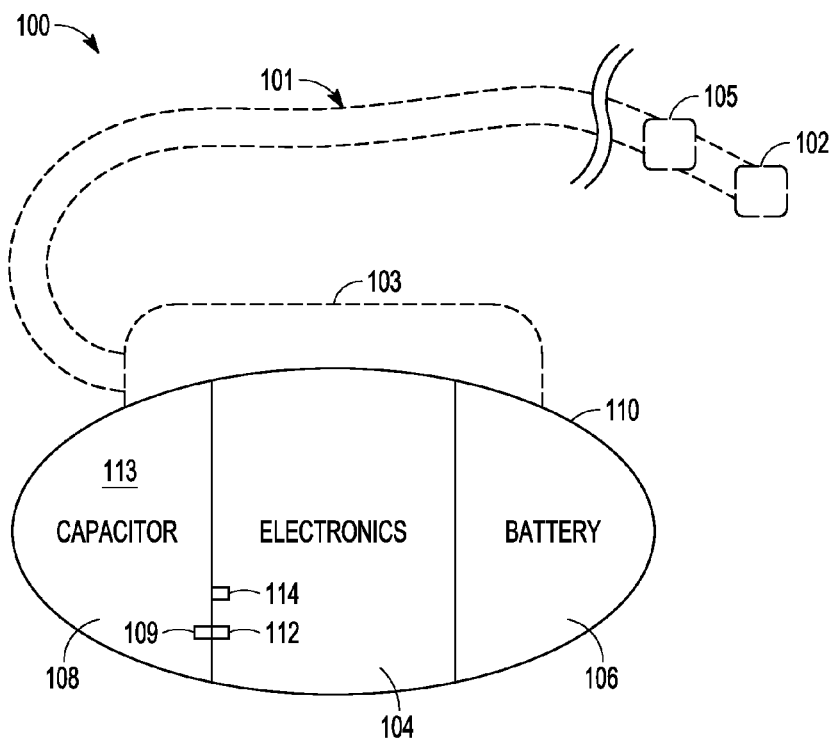
FIG. 1 shows a schematic representation of a medical system including a sintered capacitor, in accordance with one embodiment.

FIG. 1 is a schematic of a medical system 100 including a sintered capacitor, according to some embodiments. The medical system 100 represents any number of systems to provide therapeutic stimulus, such as to a heart. Examples of medical systems include, but are not limited to, implantable pacemakers, implantable defibrillators, implantable nerve stimulation devices and devices that provide stimulation from outside the body, including, but not limited to, external defibrillators.

Electronics 104 are to monitor the patient, such as by monitoring a sensor 105, and to monitor and control activity within the system 100. In some examples, the electronics 104 are to monitor a patient, diagnose a condition to be treated such as an arrhythmia, and control delivery of a stimulation pulse of energy to the patient. The electronics 104 can be powered wirelessly using an inductor. Alternatively, the electronics 104 can be powered by a battery 106. In some examples, electronics 104 are to direct small therapeutic bursts of energy to a patient from the battery 106.

For therapies, such as defibrillation, that use energy discharge rates exceeding what battery 106 is able to provide, a capacitor 108 is used. Energy from the battery 106 is controlled by the electronics 104 to charge the capacitor 108. The capacitor 108 is controlled by the electronics 104 to discharge to a patient to treat the patient. In some examples, the capacitor 108 completely discharges to a patient, and in additional examples, the capacitor is switched on to provide therapeutic energy and switched off to truncate therapy delivery.

Some examples of a medical system 100 include an optional lead system 101. In certain instances, after implantation, the lead system 101 or a portion of the lead system 101 is in electrical communication with tissue to be stimulated. For example, some configurations of lead system 101 contact tissue with a stimulation electrode 102. The lead system 101 couples to other portions of the system 100 via a connection in a header 103. Examples of the system 101 use different numbers of stimulation electrodes and/or sensors in accordance with the needs of the therapy to be performed.

Additional examples function without a lead 101. Leadless examples can be positioned in contact with the tissue to be stimulated, or can be positioned proximal to tissue to shock the tissue to be stimulated through intermediary tissue. Leadless examples can be easier to implant and can be less expensive as they do not require the additional lead components. The housing 110 can be used as an electrode in leadless configurations.

In certain embodiments, the electronics 104 include an electronic cardiac rhythm management circuit coupled to the battery 106 and the capacitor 108 to discharge the capacitor 108 to provide a therapeutic pulse, such as a defibrillation pulse. In some examples, the system 100 includes an anode and a cathode sized to deliver a pulse of at least approximately 50 joules. Other configurations can deliver larger amounts of energy. Some configurations deliver less energy, for example at least 36 joules. In some examples, the energy level is predetermined to achieve a delivered energy level mandated by a governing body or standard associated with a geographic region, such as a European country. In an additional embodiment, the anode and cathode are sized to deliver a defibrillation pulse of at least approximately 60 joules. In some examples, this is the energy level is predetermined to achieve an energy level mandated by a governing body of another region, such as the United States. In some examples, electronics 104 are to control discharge of a defibrillation pulse so that the medical system 100 delivers only the energy mandated by the region in which the system 100 is used.

One characteristic of some sintered electrode examples is that at least one anode and a cathode have a DC capacitance that is approximately 23% greater than a AC capacitance for the at least one anode and the cathode of an etched capacitor that has 74.5 microfarads per cubic centimeter. In some examples, the at least one anode and the cathode have an AC capacitance of at least 96.7 microfarads per cubic centimeter at 445 total voltage. In some examples, this is comparable to an operating voltage of about 415 volts. This is a 30% improvement over an etched capacitor that has 74.5 microfarads per cubic centimeter. Total voltage is the voltage that allows 1 milliamp of leakage per square centimeter for an electrode. Some examples are aged to 415 volts.

In certain examples, the capacitor 108 includes a capacitor case 113 sealed to retain electrolyte. In some examples, the capacitor case 113 is welded. In some instances, the capacitor case 113 is hermetically sealed. In additional examples, the capacitor case 113 is sealed to retain electrolyte, but is sealed with a seal to allow flow of other matter, such as gaseous diatomic hydrogen or a helium molecule. Some of these examples use an epoxy seal. The capacitor further includes a conductor 109 coupled to one of the electrodes of the capacitor 108. The conductor 109 sealingly extends through the capacitor case to a first terminal 112 disposed on an exterior of the capacitor case 113. A second terminal 114 can be disposed on the exterior of the capacitor case 113 and in electrical communication with the other electrode of the capacitor 108. The first terminal 112 and the second terminal 114 are electrically isolated from one another.

A hermetically sealed device housing 110 is used to house components, such as the battery 106, the electronics 104, and the capacitor 108. Hermeticity is provided by welding components into the hermetically sealed device housing 110, in some examples. Other examples bond portions of the housing 110 together with an adhesive such as a resin based adhesive such as epoxy. Accordingly, some examples of the housing 110 include an epoxy sealed seam or port. Several materials can be used to form housing 110, including, but not limited to, titanium, stainless steel, nickel, a polymeric material, or combinations of these materials. In various examples, the housing 110 and the case 113 are biocompatible.

The capacitor 108 is improved by the present electrode technology in part because it can be made smaller and with less expense and a variety of shapes and configurations. The improvement provided by these electrodes is pertinent to any application where high-energy, high-voltage, or space-efficient capacitors are desirable, including, but not limited to, capacitors used for photographic flash equipment. The present subject matter extends to energy storage devices that benefit from high surface area sintered electrodes including, but not limited to, aluminum. The electrodes described here can be incorporated into cylindrical capacitors that are wound, in addition to stacked capacitors.

Figure 2:
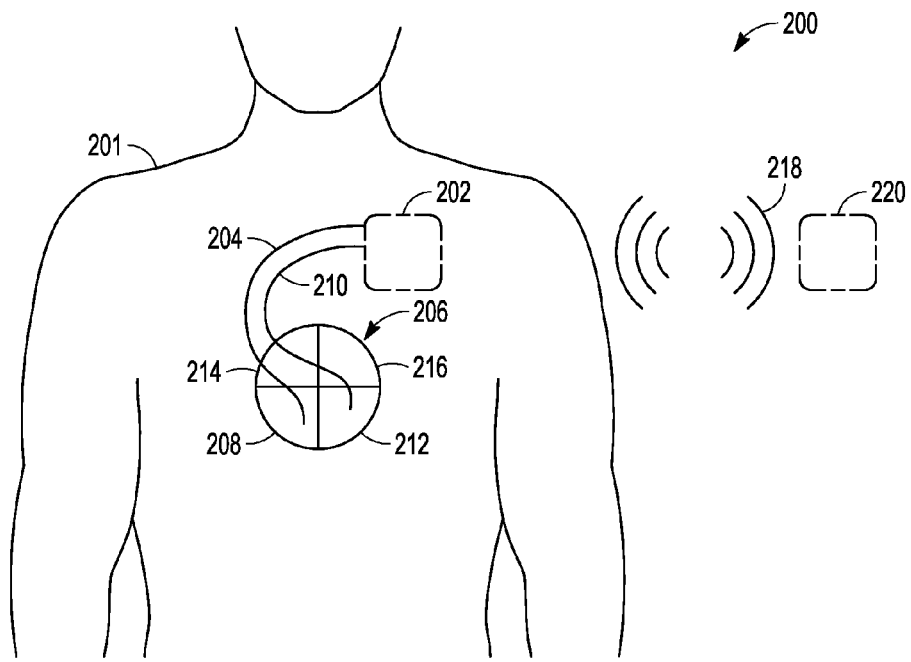
FIG. 2 shows an implanted medical system including a sintered capacitor, in accordance with one embodiment.

FIG. 2 is an implanted medical system 200, implanted in a patient 201, and including a sintered capacitor, according to some embodiments. The system includes a cardiac rhythm management device 202 coupled to a first lead 204 to extend through the heart 206 to the right ventricle 208 to stimulate at least the right ventricle 208. The system also includes a second lead 210 to extend through the heart 206 to the left ventricle 212. In various embodiments, one or both of the first lead 204 and the second lead 210 include electrodes to sense intrinsic heart signals and to stimulate the heart. The first lead 204 is in direct contact (e.g., touching) with the right atrium 214 and the right ventricle 208 to sense and/or stimulate both those tissue regions. The second lead 210 is in direct contact with the left atrium 216 and the left ventricle 212 to sense and/or stimulate both those tissue regions. The cardiac rhythm management device 202 uses the lead electrodes to deliver energy to the heart, either between electrodes on the leads or between one or more lead electrodes and the cardiac rhythm management device 202. Some embodiments can include epicardially or subcutaneously placed leads. In some examples, the cardiac rhythm management device 202 is programmable and wirelessly communicates 218 programming information with a programmer 220. In some examples, the programmer 220 wirelessly 218 charges an energy storage device of the cardiac rhythm management device 202.

The present system allows for different concepts for the design of high voltage aluminum electrolytic capacitors. As will be discussed, the present system allows for reducing assembly time and cost by providing shapes that allow for ease of assembly with reduction of precise robotic assembly.

Figure 3:
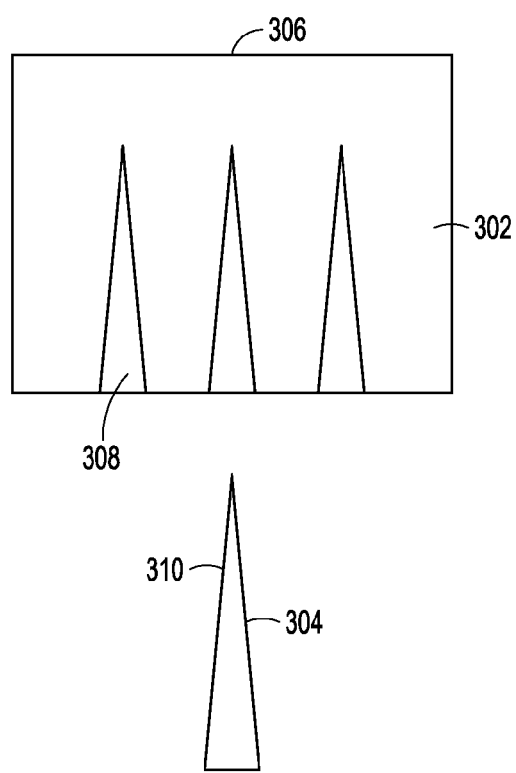
FIG. 3 shows a sintered anode and sintered cathode, in accordance with one embodiment.

FIG. 3 shows a sintered anode 302 and a sintered cathode 304 for a capacitor, in accordance with one embodiment. The sintered anode 302 includes a sintered portion 306 and one or more mating portions, such as void spaces 308. The sintered cathode 304 can have a shape that mates with the void space 308 of the sintered anode 302 such that the sintered cathode 304 matingly fits in the void space 308 of the sintered anode. In this example, both the sintered anode 302 and the sintered cathode 304 have non-rectangular shapes. By using sintered cathodes 304, the sintered cathodes 304 can be smaller than previous and can be shaped and configured to interlock with the various sintered anode shapes. Moreover, using sintering for the anodes and cathodes helps reduce the cost and scrap of anode and cathode materials, since the electrodes do not need to be cut from a web. In addition, the sintered anode 302 and the sintered cathode 304 can include standalone slugs with the sintered portion being monolithic without a substrate.

In various examples, the void space 308 can be conical and the sintered cathode 304 can be conical. In one example, the void space 308 of the sintered anode 312 can be shaped like a fin and the sintered cathode 304 can have a fin shape. In one example, the capacitor can include a plurality of sintered cathodes 304 forming a bed-of-nails type structure. The sintered anode 302 can then be dropped over the bed of nails structure. Such shapes and structures allow for ease of assembly with lower complexity.

In one example, the sintered cathode 304 can include a high capacitance coating on an outer surface 310 of the sintered cathode 304. For example, an ALD (atomic layer deposition) coating of titanium can be applied to a portion of, or all of, the outer surface 306. Other examples can include ruthenium, hafnium, etc. The high capacitance coating will provide a much higher capacitance than just aluminum.

Figure 4:
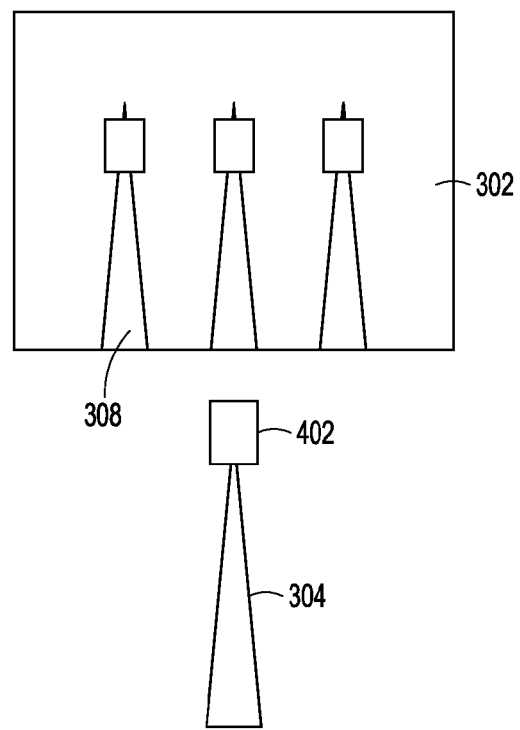
FIG. 4 shows a sintered anode and sintered cathode, in accordance with one embodiment.
Figure 5:
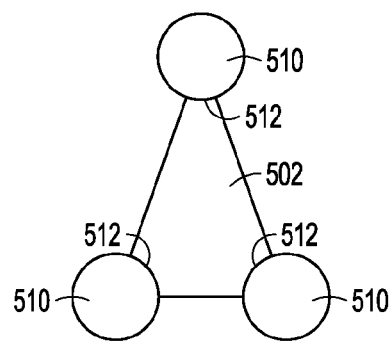
FIG. 5 shows a sintered anode and sintered cathode, in accordance with one embodiment.
Figure 6:
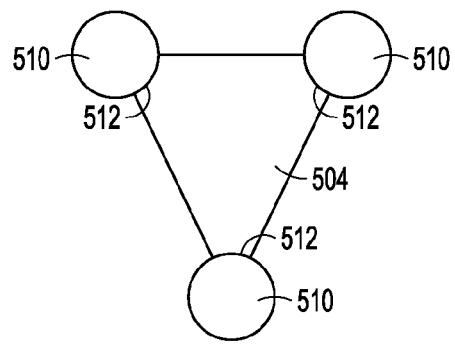
FIG. 6 shows a sintered anode and sintered cathode, in accordance with one embodiment.

FIG. 4 shows the sintered anode 302 and the sintered cathode 304 and further includes a separator 402 between the sintered anode 302 and the sintered cathode 304. In an example, the separator 402 can include a high dielectric polymer directly applied to an outer surface of the sintered cathode 304. For example, a high dielectric and hydrophilic polymer can be electro-spun directly onto the sintered cathode surface. In one example, a microsphere coating applied to the surface of the sintered cathode 304 can be the separator 402. Omitting a conventional separate paper separator can aid manufacturing because there are fewer assembly steps. Moreover, the separator 402 allows for complex cathode shapes to be used that would not be feasible using only paper separators. In some examples, the separator can be applied to the sintered anode 302.

FIGS. 5-8 shows various shapes and configurations for sintered anodes 502 and 504 and sintered cathodes 510, in accordance with some embodiments. In this example, the sintered anodes 502 and 504 are triangular in shape and have one or more mating portions such as void spaces comprising a rounded cut-out 512 at one or more corners of the triangular sintered anode 502, 504. The sintered cathodes 510 can include a cylindrical shape similar to the shape of the void spaces of anodes 502, 504. As discussed above, the sintered cathodes 510 can have an electro-spun (or microsphere) coating on the outer surface of the cylindrical shape to act as the separator.

Figure 7:
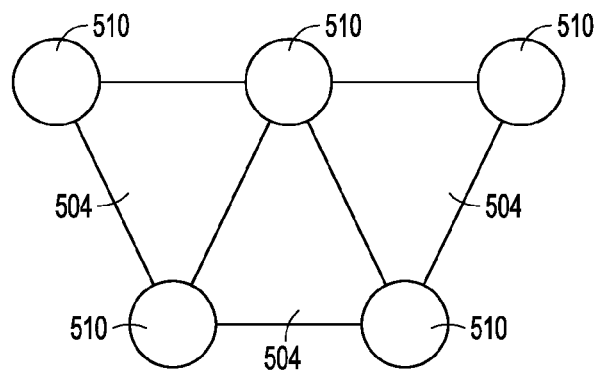
FIG. 7 shows a sintered anode and sintered cathode, in accordance with one embodiment.
Figure 8:
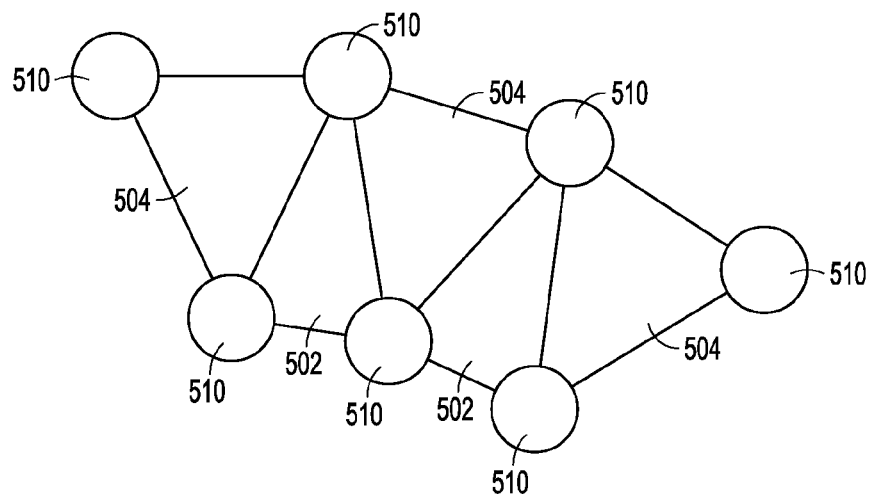
FIG. 8 shows a sintered anode and sintered cathode, in accordance with one embodiment.

The sintered anodes 502, 504 can be arranged together in a side by side configuration in various patterns with a plurality of cylindrical cathodes 302 located at the rounded out corners in the void spaces of each of the plurality of sintered anodes 502, 504. For example, FIG. 7 shows similarly shaped sintered anodes 504 arranged in top/bottom alternating pattern. FIG. 8 shows an alternating pattern, but using the thinner anodes 502 to allow the overall shape to be shaped and structured as desired. In various embodiments, many other patterns can be formed using the sintered anodes 502, 504.

Figure 9:
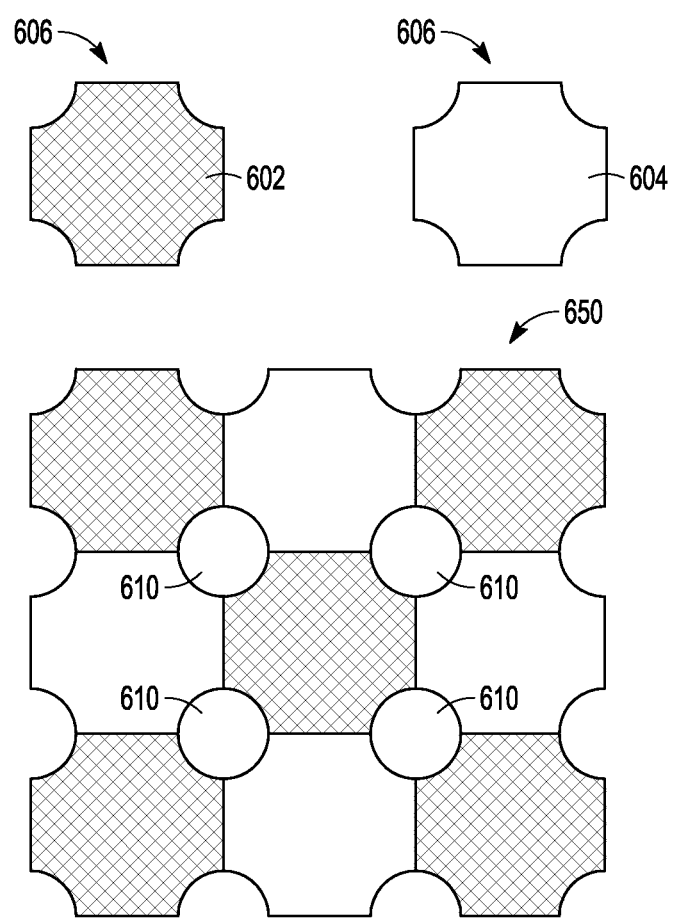
FIG. 9 shows a sintered anode and sintered cathode, in accordance with one embodiment.

FIG. 9 shows sintered anodes 602, 604 and sintered cathodes 610, in accordance with one embodiment. The sintered anodes 602 and 604 can be generally rectangular with mating portion such as void spaces, including cut-outs 606 at one or more corners of the sintered anode 602, 604. As above, the sintered cathodes 610 can be cylindrical in shape and can include a dielectric coating to act as a separator. The sintered anodes 602, 604 can be arranged in various patterns and the sintered cathodes 610 fit matingly into the combined void spaces formed by the cut-outs 606. Such "Lego™-like" or "puzzle-like" structures allow for the creation of configurations that do not require the sandwich-like stacking of current capacitors.

Figure 10:
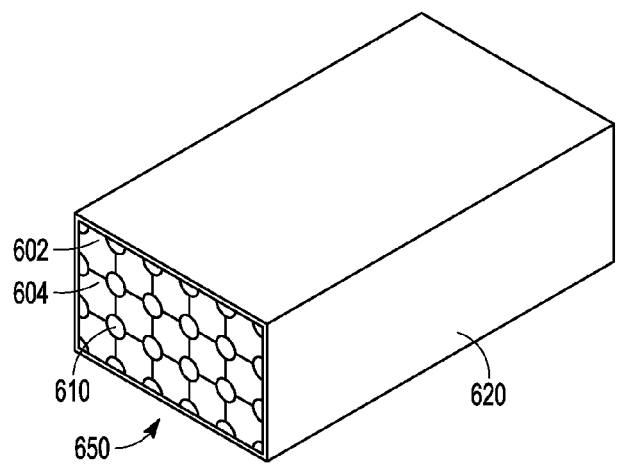
FIG. 10 shows a perspective view of sintered anode and sintered cathodes of FIG. 9, in accordance with one embodiment.
Figure 11:
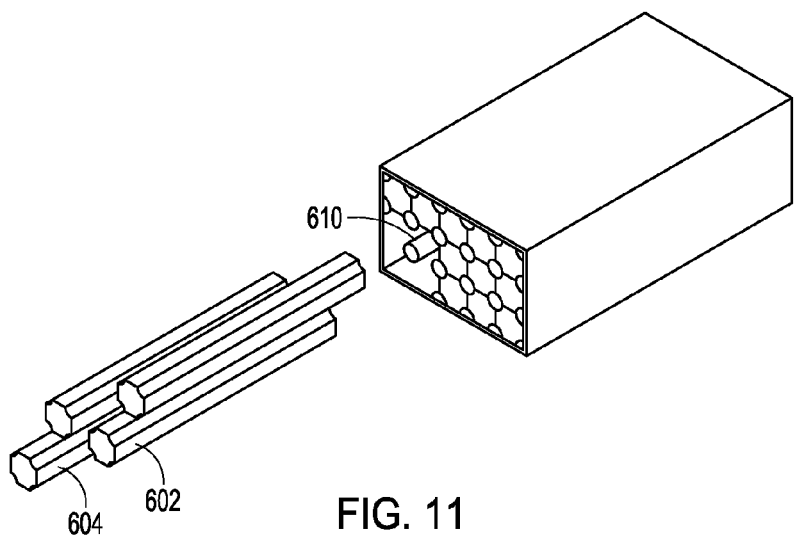
FIG. 11 shows a perspective view of sintered anode and sintered cathodes of FIG. 9, in accordance with one embodiment.

FIGS. 10 and 11 show a perspective view of sintered anodes 602, 604 and the sintered cathodes 610 as inserted into a capacitor case 620.

Figure 12:
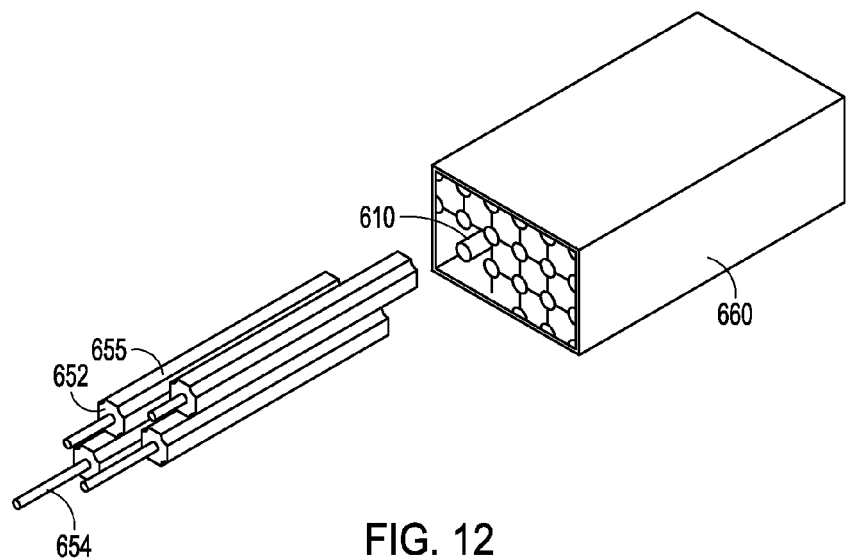
FIG. 12 shows a perspective view of a sintered anode and sintered cathode, in accordance with one embodiment.

FIG. 12 shows a perspective view of a sintered anode 655 having a central hole 652 and a sintered cathode 654 and further sintered cathodes 610, in accordance with one embodiment. This example is similar to the embodiment of FIGS. 9-11, but further includes a cylindrical sintered cathode 654 inserted into hole 652, with cathodes 610 located at the corners of the anodes 655. The anodes 655 and cathodes 654 and 610 are inserted into a capacitor case 660.

Figure 13:
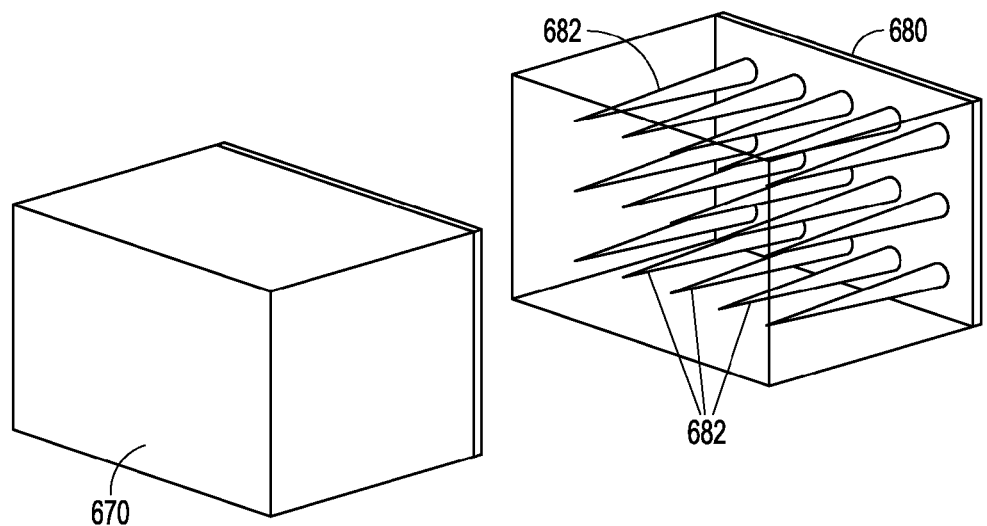
FIG. 13 shows a perspective view of a sintered anode and sintered cathode, in accordance with one embodiment.
Figure 14:
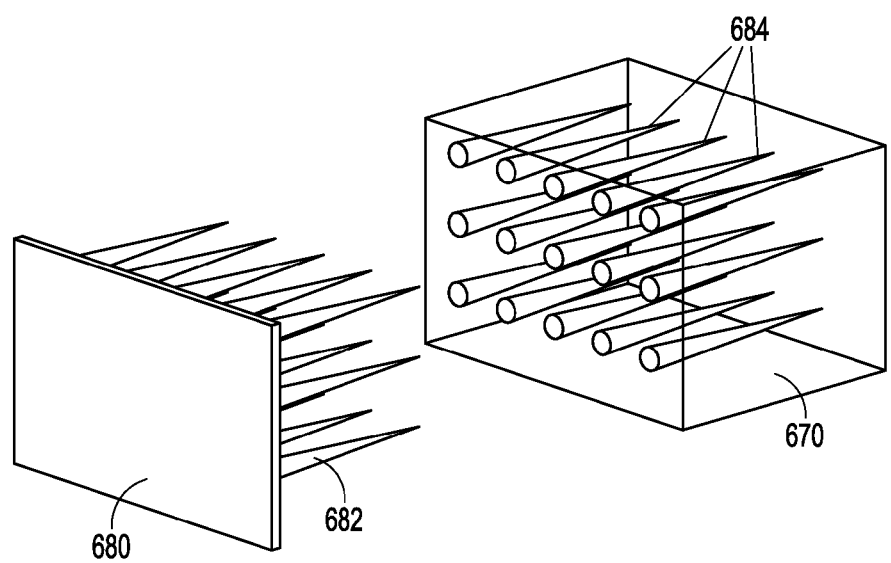
FIG. 14 shows a perspective view of a sintered anode and sintered cathode, in accordance with one embodiment.

FIGS. 13 and 14 show front and rear perspective views of a sintered anode 670 and sintered cathode 680, in accordance with one embodiment. In this example, the sintered cathode includes a plurality of conical cathode peaks 682, having a bed-of-nails structure. The anode 670 includes a plurality of mating portions, such as conical void spaces 684 that correspond to the cathode peaks 682. Such shapes and structures allow for ease of assembly with lower complexity.

Figure 15:
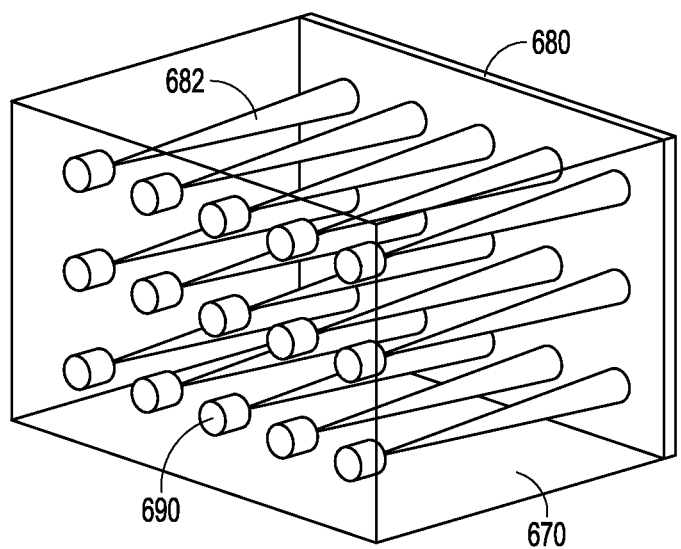
FIG. 15 shows a perspective view of a sintered anode and sintered cathode, in accordance with one embodiment.
Figure 16:
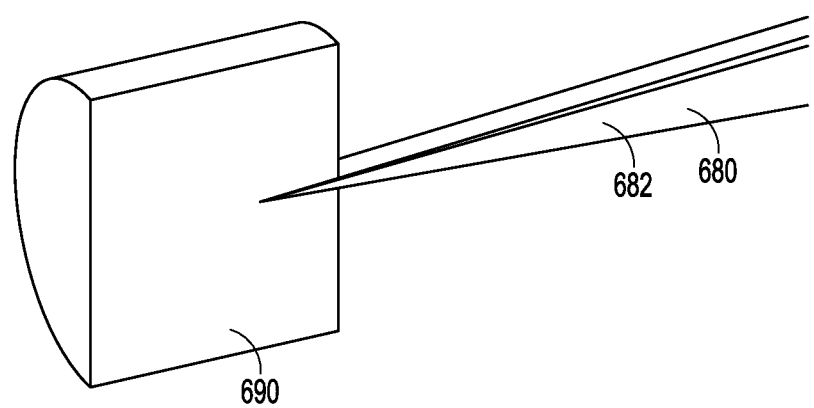
FIG. 16 shows a perspective view of a sintered anode and sintered cathode, in accordance with one embodiment.

FIGS. 15 and 16 show the sintered anode 670 and the sintered cathode 680 assembled with a separator 690 located on each of peaks 682 of the cathode 680. As discussed above, the separator 690 can include a high dielectric polymer directly applied to an outer surface of the sintered cathode 680. For example, a high dielectric and hydrophilic polymer can be electro-spun directly onto the sintered cathode surface. In one example, a microsphere coating applied to the surface of the sintered cathode 680 can be the separator 690.

Figure 17:
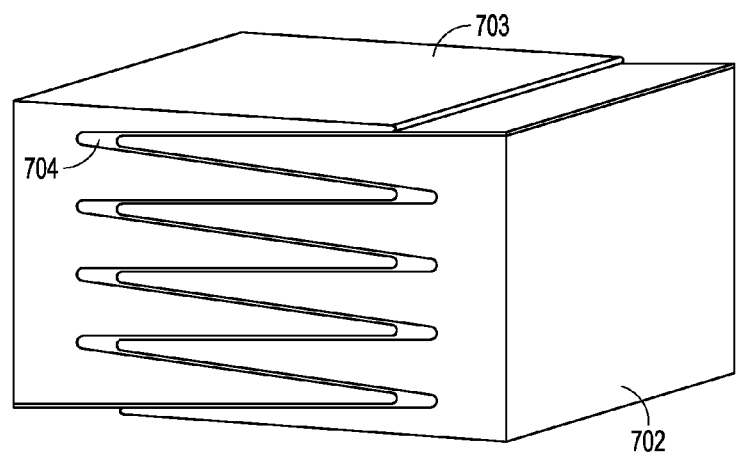
FIG. 17 shows a perspective view of a sintered anode and sintered cathode, in accordance with one embodiment.
Figure 18:
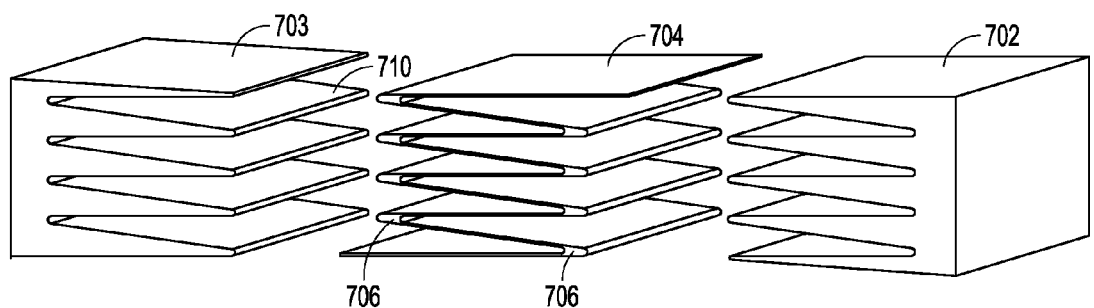
FIG. 18 shows a perspective view of a sintered anode and sintered cathode, in accordance with one embodiment.

FIGS. 17 and 18 show a perspective view of sintered anodes 702 and 703 and sintered cathode 704, in accordance with one embodiment. In FIG. 17 the anodes 702, 703 and cathode 704 are assembled. FIG. 18 shows an exploded view of anodes 702, 703 and cathode 704. In this example the cathode 704 includes a serpentine fan-like shape with peaks 706 formed on each side of the cathode 704. Each of anodes 702, 703 include mating portions, such as void spaces 710 that are dimensioned to receive the peaks 706. As previously discussed, a high dielectric and hydrophilic polymer can be electro-spun directly onto the sintered cathode surface or a microsphere coating can be applied as a separator.

In constructing the various capacitors discussed above, an anode can be formed by sintering anode material into a non-rectangular shape having a mating portion, such as a void space. A cathode can be formed by sintering cathode material into a shape that mates with the void space of the sintered anode such that the sintered cathode matingly fits in the void space of the sintered anode. As noted, a separator can be applied to a surface of the cathode (or the anode). The sintered anode and cathode can then be disposed into a capacitor case, or they can be assembled directly into the capacitor case. In one example, the sintered cathodes can be formed directly on the capacitor case and then the anode can be placed over or around the cathodes depending on the configuration desired.

In any of the examples herein, a high dielectric and hydrophilic polymer can be electro-spun directly onto the sintered cathode surface. In some examples, a microsphere coating applied to the surface of the sintered cathode can be the separator. Omitting a conventional separate paper separator can aid manufacturing because there are fewer assembly steps. In some examples, the separator can be applied to the sintered anode. For some embodiments, a conventional paper separator can be used, depending on the geometry of the sintered anodes and cathodes.

In any of the examples herein, the sintered cathode can include a high capacitance coating on an outer surface of the sintered cathode. For example, an ALD (atomic layer deposition) coating of titanium can be applied to a portion of, or all of, the outer surface. Other examples can include ruthenium, hafnium, etc. The high capacitance coating will provide a much higher capacitance than just aluminum.

This application is intended to cover adaptations or variations of the present subject matter. It is to be understood that the above description is intended to be illustrative and not restrictive. The scope of the present subject matter should be determined with reference to the appended claims, along with the full scope of legal equivalents to which such claims are entitled.

What is claimed is:
1. An apparatus, comprising:
a capacitor case sealed to retain electrolyte;
a plurality of sintered anodes disposed in the capacitor case, each sintered anode having a shape wherein the sintered anode includes a mating portion;

a conductor coupled to the sintered anode, the conductor sealingly extending through the capacitor case to a terminal disposed on an exterior of the capacitor case;

a sintered cathode disposed in the capacitor case, the sintered cathode having a shape that mates with the mating portion of the sintered anode such that the sintered cathode matingly fits in the mating portion of the sintered anode;

wherein the mating portion of each of the sintered anodes includes rounded cut-outs at one or more corners of the sintered anode, and wherein the sintered cathode has a cylindrical shape configured to be received by the rounded cut-out such that adjacent sintered anodes form a combined rounded void at their respective corners to receive the cylindrical sintered cathode;

a separator between the sintered anode and the sintered cathode; and a second terminal disposed on the exterior of the capacitor case and in electrical communication with the sintered cathode, with the terminal and the second terminal electrically isolated from one another.

2. The apparatus of claim 1, wherein the sintered anode has a non-rectangular shape.

3. The apparatus of claim 1, wherein the sintered cathode has a non-rectangular shape.

4. The apparatus of claim 1, wherein each sintered anode has a rectangular shape with a cut-out at each of the four corners of the anode.

5. The apparatus of claim 4, further including a plurality of cylindrical sintered cathodes, wherein each cathode is positioned at a common corner of four adjacent sintered anodes.

6. The apparatus of claim 1, wherein the sintered anode has a triangular shape with the rounded cut-outs at the three corners of the triangular shape.

7. The apparatus of claim 6, including a plurality of sintered anodes having triangular shapes and arranged together in a side by side configuration with a plurality of cylindrical cathodes located at the rounded out corners of each of the plurality of sintered anodes.

8. The apparatus of claim 1, wherein the separator includes a high dielectric polymer directly applied to an outer surface of the sintered cathode.

9. The apparatus of claim 1, wherein the sintered cathode includes a high capacitance coating on an outer surface.

10. The apparatus of claim 1, wherein the sintered anode and the sintered cathode comprise standalone slugs that includes the sintered portion, with the sintered portion being monolithic.

11. A system, comprising:
a hermetically sealed device housing;
a battery disposed in the hermetically sealed device housing;
a capacitor disposed in the hermetically sealed device housing, the capacitor comprising:
  a capacitor case sealed to retain electrolyte;
  a plurality of sintered anodes disposed in the capacitor case, each sintered anode having a shape wherein the sintered anode includes a void space;
  a conductor coupled to the sintered anode, the conductor sealingly extending through the capacitor case to a terminal disposed on an exterior of the capacitor case;
  a sintered cathode disposed in the capacitor case, the sintered cathode having a shape that mates with the void space of the sintered anode such that the sintered cathode matingly fits in the void space of the sintered anode;
  wherein the mating portion of each of the sintered anodes includes rounded cut-outs at one or more corners of the sintered anode, and wherein the sintered cathode has a cylindrical shape configured to be received by the rounded cut-out such that adjacent sintered anodes form a combined rounded void at their respective corners to receive the cylindrical sintered cathode;
  a separator between the sintered anode and the sintered cathode; and
  a second terminal disposed on the exterior of the capacitor case and in electrical communication with the sintered cathode, with the terminal and the second terminal electrically isolated from one another, and
an electronic cardiac rhythm management circuit coupled to the battery and the capacitor and adapted to discharge the capacitor to provide a therapeutic pulse.

12. The apparatus of claim 11, wherein each sintered anode has a rectangular shape with a cut-out at each of the four corners of the anode.

13. The apparatus of claim 11, wherein the sintered anode has a triangular shape with the rounded cut-outs at the three corners of the triangular shape.

14. A method, comprising:
sintering anode material into a non-rectangular shape having a void space;
sintering cathode material into a shape that mates with the void space of the sintered anode such that the sintered cathode matingly fits in the void space of the sintered anode;
wherein the mating portion of sintered anode includes rounded cut-outs at one or more corners of the sintered anode, and wherein the sintered cathode has a cylindrical shape configured to be received by the rounded cut-out such that adjacent sintered anodes form a combined rounded void at their respective corners to receive a common cathode;
disposing a separator between the sintered anode and the sintered cathode; and
disposing the sintered anode and sintered cathode into a capacitor case.

15. The method of claim 14, wherein the separator includes a high dielectric polymer directly applied to an outer surface of the sintered cathode.

16. The method of claim 14, wherein each sintered anode has a rectangular shape with a cut-out at each of the four corners of the anode.

17. The method of claim 16, wherein the sintered anode has a triangular shape with the rounded cut-outs at the three corners of the triangular shape.

* * * * *